(12) United States Patent
Corson

(10) Patent No.: US 7,205,154 B2
(45) Date of Patent: Apr. 17, 2007

(54) CALIBRATING ARRAY SCANNERS

(75) Inventor: John F. Corson, Stanford, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 906 days.

(21) Appl. No.: 10/066,157

(22) Filed: Jan. 31, 2002

(65) Prior Publication Data

US 2003/0143751 A1   Jul. 31, 2003

(51) Int. Cl.
*G01N 30/00* (2006.01)

(52) U.S. Cl. ............................. 436/164; 436/8; 422/50; 422/82.05

(58) Field of Classification Search ................. 422/50, 422/82.05, 82.09; 436/8, 164, 166
See application file for complete search history.

(56) References Cited

U.S. PATENT DOCUMENTS

| | | | |
|---|---|---|---|
| 5,315,375 A | 5/1994 | Allen | |
| 5,376,804 A | 12/1994 | Coleman | |
| 5,532,874 A | 7/1996 | Stein | |
| 5,763,870 A | 6/1998 | Sadler et al. | |
| 5,812,272 A * | 9/1998 | King et al. ................. | 356/445 |
| 5,945,679 A | 8/1999 | Dorsel et al. | |
| 6,043,880 A | 3/2000 | Andrews et al. | |
| 6,130,745 A | 10/2000 | Manian et al. | |
| 6,236,456 B1 | 5/2001 | Giebeler et al. | |
| 6,262,838 B1 | 7/2001 | Montagu | |

2001/0033414 A1   10/2001   Yahiro

FOREIGN PATENT DOCUMENTS

| | | |
|---|---|---|
| EP | 0902271 A2 | 3/1999 |
| EP | 1091229 A2 | 4/2001 |
| JP | 09203865 | 8/1997 |
| JP | 09304701 | 11/1997 |
| JP | 10153529 | 6/1998 |
| JP | 10232342 | 9/1998 |
| WO | WO 99/47964 | 9/1999 |
| WO | WO 01/59503 | 8/2001 |

OTHER PUBLICATIONS

European Patent Office Communication dated Nov. 7, 2003 with enclosure of European Search Report and Annex to the EP Search Report for counterpart EP Application No. 03/25/0635.

* cited by examiner

*Primary Examiner*—Jill Warden
*Assistant Examiner*—Samuel P. Siefke

(57) ABSTRACT

A method of using a chemical array reader, chemical array readers, and computer program products for use with a chemical array reader. The chemical array reader may include a holder to mount an array and hold the array at a reading position. A light system illuminates a mounted array when at a reading position. A detection system having a focal plane, to detect light from different regions across the array emitted in response to the illumination, when at the reading position, and which generates a resulting signal for each of the regions across the array. An autofocus system which detects and reduces offset between the different regions of an array at the reading position and a determined position of the focal plane.

26 Claims, 5 Drawing Sheets

CALIBRATING ARRAY SCANNERS

FIELD OF THE INVENTION

This invention relates to arrays, particularly biopolymer arrays such as DNA or protein arrays, which are useful in diagnostic, screening, gene expression analysis, and other applications.

BACKGROUND OF THE INVENTION

Polynucleotide arrays (such as DNA or RNA arrays) and peptide array, are known and may be used, for example, as diagnostic or screening tools. Such arrays include regions (sometimes referenced as spots or features) of usually different sequence polynucleotides or peptides arranged in a predetermined configuration on a substrate. The array is "addressable" in that different features have different predetermined locations ("addresses") on a substrate carrying the array.

Biopolymer arrays can be fabricated using in situ synthesis methods or deposition of the previously obtained biopolymers. The in situ fabrication methods include those described in U.S. Pat. No. 5,449,754 for synthesizing peptide arrays, and in U.S. Pat. No. 6,180,351 and WO 98/41531 and the references cited therein for polynucleotides. In situ methods also include photolithographic techniques such as described, for example, in WO 91/07087, WO 92/10587, WO 92/10588, and U.S. Pat. No. 5,143,854. The deposition methods basically involve depositing biopolymers at predetermined locations on a substrate which are suitably activated such that the biopolymers can link thereto. Biopolymers of different sequence may be deposited at different feature locations on the substrate to yield the completed array. Procedures known in the art for deposition of biopolymers, particularly DNA such as whole oligomers or cDNA, are described, for example, in U.S. Pat. No. 5,807,522 (touching drop dispensers to a substrate), and in PCT publications WO 95/25116 and WO 98/41531, and elsewhere (use of a pulse jet in the form of a piezoelectric inkjet head).

Further details of large scale fabrication of biopolymer arrays by depositing either previously obtained biopolymers or by the in situ method, are disclosed in U.S. Pat. No. 6,242,266, U.S. Pat. No. 6,232,072, U.S. Pat. No. 6,180,351, and U.S. Pat. No. 6,171,797.

In array fabrication, the quantities of DNA available for the array are usually very small and expensive. Sample quantities available for testing are usually also very small and it is therefore desirable to simultaneously test the same sample against a large number of different probes on an array. These conditions require the manufacture and use of arrays with large numbers of very small, closely spaced features.

The arrays, when exposed to a sample, will exhibit a binding pattern. The array can be read by observing this binding pattern by, for example, labeling all targets such as polynucleotide targets (for example, DNA), in the sample with a suitable label (such as a fluorescent compound), scanning an illuminating beam across the array and accurately observing the fluorescent signal from the different features of the array. Assuming that the different sequence polynucleotides were correctly deposited in accordance with the predetermined configuration, then the observed binding pattern will be indicative of the presence and/or concentration of one or more polynucleotide components of the sample. Peptide or arrays of other chemical moieties can be used in a similar manner. Techniques and apparatus for scanning chemical arrays are described, for example, in U.S. Pat. No. 5,763,870 and U.S. Pat. No. 5,945,679. Apparatus which reads an array by scanning an illuminating beam by the foregoing technique are often referred to as scanners and the technique itself often referred to as scanning.

Array scanners typically use a laser beam as a light source, which is scanned over the array features. A detector (typically a fluorescence detector) with a very high light sensitivity is normally desirable to achieve maximum signal-to-noise in detecting hybridized molecules, particularly in array scanners used for DNA sequencing or gene expression studies. At present, photomultiplier tubes ("PMTs") are still the detector of choice although charge coupled devices ("CCDs") can also be used. PMTs are typically used for temporally sequential scanning of array features, while CCDs permit scanning many features in parallel (for example, one line of features simultaneously, in which case an illuminating line may be used).

When a sample component only weakly binds to an array feature (due to a low concentration of that component in the sample) the resulting fluorescence signal from that feature will be low. To be able to detect such low signal features, it is important that the detection of fluorescence from the substrate be kept as low as possible to minimize the resulting noise and maintain the signal to noise ratio as high as possible. One previously known way of improving signal/noise ration is by providing a scanner with a relatively narrow depth of focus (that is, it has a focal plane) so that the coincidental reading of fluorescence from the substrate will be kept low. While this is beneficial, it is always desirable to find other means of improving signal/noise ratio and to thereby enhance scanner sensitivity.

SUMMARY OF THE INVENTION

The present invention then, provides a chemical array reader, which includes a holder to mount an array, a calibration member, and a light system to illuminate the calibration member or mounted array when either is at a reading position. A carriage alternately positions the mounted array and calibration member into the reading position. A detection system having a focal plane, detects light from one or more regions of the calibration member and from different regions across the array emitted in response to the illumination, when either is in the reading position, and which generates a resulting signal for each of the one or more regions of the calibration member and for each of the regions across the array.

The chemical array reader may further be provided with an adjuster and an autofocus system. The adjuster adjusts the position of the calibration member (and optionally, similarly simultaneously adjusts the array position), when in the reading position, relative to the focal plane, such that the position of the the focal plane can be determined from the resulting detection system signal. The autofocus system senses and reduces offset between the different regions of the array, when in the reading position, and the determined focal plane position, and may reduce the offset by adjusting the relative position of the array and determined position of the focal plane using the adjuster. This adjustment can be used to keep the calibration member (or array) in the desired focal plane as the scanner reads different regions, even if the member (or array) are not flat (that is, have imperfections in their planarity). The autofocus system may also include a detector which detects the offset as an offset signal, and may further include a processor which receives the offset signal and controls the adjuster to reduce (and ideally, minimize) the offset. Alternatively or in addition to the adjuster and autofocus system, the detection system may detect light at multiple wavelengths from the calibration member or array, when either is at the reading position, and generate a resulting signal for each of the multiple detected wavelengths for the one or more regions of the calibration member and for each of the regions across the array.

The reader may also include a processor which determines the focal plane position from the light detected at various adjustments of the calibration member. In one arrangement, the focal position may be determined based on a variation in detected light amplitude from the same region of the calibration member or from multiple regions of the calibration member from which the detected light is the same when at the focal plane, which variation results from the adjustment of the calibration member relative to the focal plane. The processor may also control the adjuster to vary the adjustment. The processor may further calibrate a sensitivity of the detection system from detection system signals generated from the calibration member, and may perform this calibration at each of multiple detected wavelengths from the detection system signal generated from the calibration member at that wavelength. The calibration member may be selected such that the emitted light is the same from each of detected regions of the calibration member (for example, by the calibration member having all of the detected regions located in a region which uniformly emits light in response to the illumination).

The reader may be arranged such that the light system illuminates a region and the detection system detect from a region, with the reader also including a scan system to simultaneously scan the illuminated and detected regions across the different regions of the array when at the reading position. The scan system may also scan the illuminated and detected regions across different regions of the calibration member when at the reading position, such that the detection system generates a resulting signal for each of the different regions across the calibration member.

The present invention further provides a method resulting from using a chemical array reader of any of the types described above, either with or without the carriage present. The method includes positioning a calibration member at the reading position so as to receive illumination from the light system and emit light in response thereto, which emitted light is detected by the detection system to generate a resulting calibration signal. A position of the calibration member, when in the reading position, is adjusted relative to the focal plane. The position of the focal plane is determined from the light detected at various adjustments. For example, the calibration member position nearest (including being at) the position which produces the maximum calibration signal and at which the calibration signal has the lowest variation with respect to position changes, (that is, where the calibration signal is most "flat" near the maximum) may be taken as the determined focal plane position. The method may also include reading one or more arrays, by positioning each array at the reading position such that the detection system detects light from different regions across the array emitted in response to the illumination, and generates a resulting signal for each of the regions across the array.

Another aspect of the present invention provides a computer program product for use with a chemical array reader of any of the types described herein, which also includes a processor communicating with the autofocus and detection systems. The computer program product comprises a computer readable storage medium having a computer program stored thereon which, when loaded into the processor, executes a method as describe herein. Such a method may include adjusting the position of the calibration member relative to the focal plane, and determining the focal plane position from the resulting detection system signals at various adjustments of the calibration member.

While the methods and apparatus have been described in connection with arrays of various moieties, such as polynucleotides or DNA, it will be understood throughout this description that other moieties can be used and may include any chemical moieties such as other biopolymers.

The present invention can provide any one or more of the following or other benefits. For example,

BRIEF DESCRIPTION OF THE DRAWINGS

Embodiments of the invention will now be described with reference to the drawings, in which.

To facilitate understanding, the same reference numerals have been used, where practical, to designate similar elements that are common to the FIGS.

DETAILED DESCRIPTION OF THE INVENTION

Figure 1:
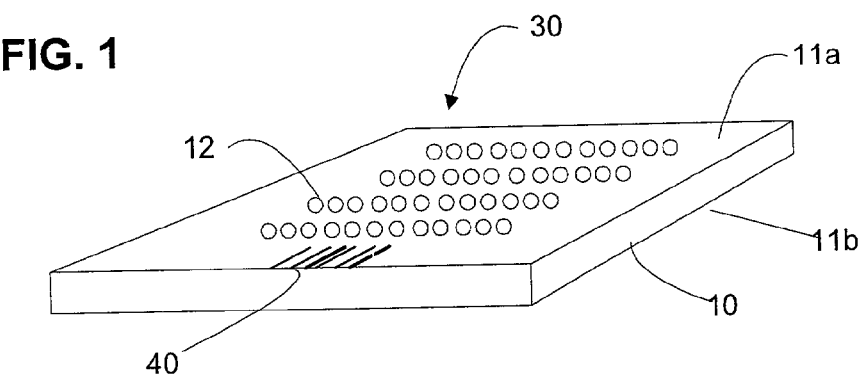
FIG. 1 is a perspective view of an array package including a substrate carrying a typical array, as may be used in the present invention.

In the present application, unless a contrary intention appears, the following terms refer to the indicated characteristics. A "biopolymer" is a polymer of one or more types of repeating units. Biopolymers are typically found in biological systems and particularly include polysaccharides (such as carbohydrates), and peptides (which term is used to include polypeptides and proteins) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948,902 and references cited therein (all of which are incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

An "array", unless a contrary intention appears, includes any one-, two- or three-dimensional arrangement of addressable regions bearing a particular chemical moiety or moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

When one item is indicated as being "remote" from another, this is referenced that the two items are at least in different buildings, and may be at least one mile, ten miles, or at least one hundred miles apart. "Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top", "upper", and "lower" are used in a relative sense only. A "region" refers to any finite small area on the array that can be illuminated and any resulting fluorescence therefrom simultaneously (or shortly thereafter) detected, for example a pixel.

A "processor" references any hardware and/or software combination which will perform the functions required of it. For example, any processor herein may be a programmable digital microprocessor such as available in the form of a mainframe, server, or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic or optical disk may carry the programming, and can be read by a suitable disk reader communicating with each processor at its corresponding station. Reference to a singular item, includes the possibility that there are plural of the same items present. "May" means optionally. Methods recited herein may be carried out in any order of the recited events which is logically possible, as well as the recited order of events. All patents and other references cited in this application, are incorporated into this application by reference except insofar as they may conflict with those of the present application (in which case the present application prevails).

Figure 2:
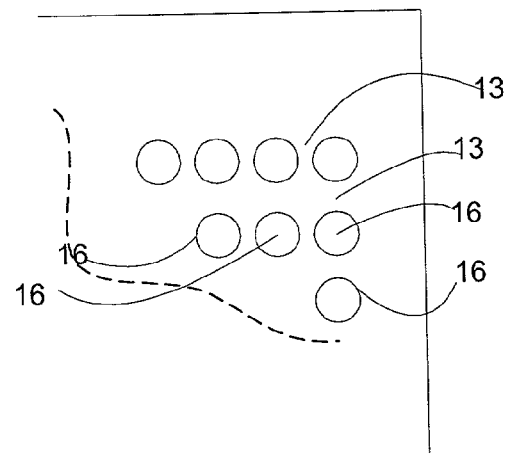
FIG. 2 is an enlarged view of a portion of FIG. 1 showing some of the identifiable individual regions of a single array of FIG. 1.
Figure 3:
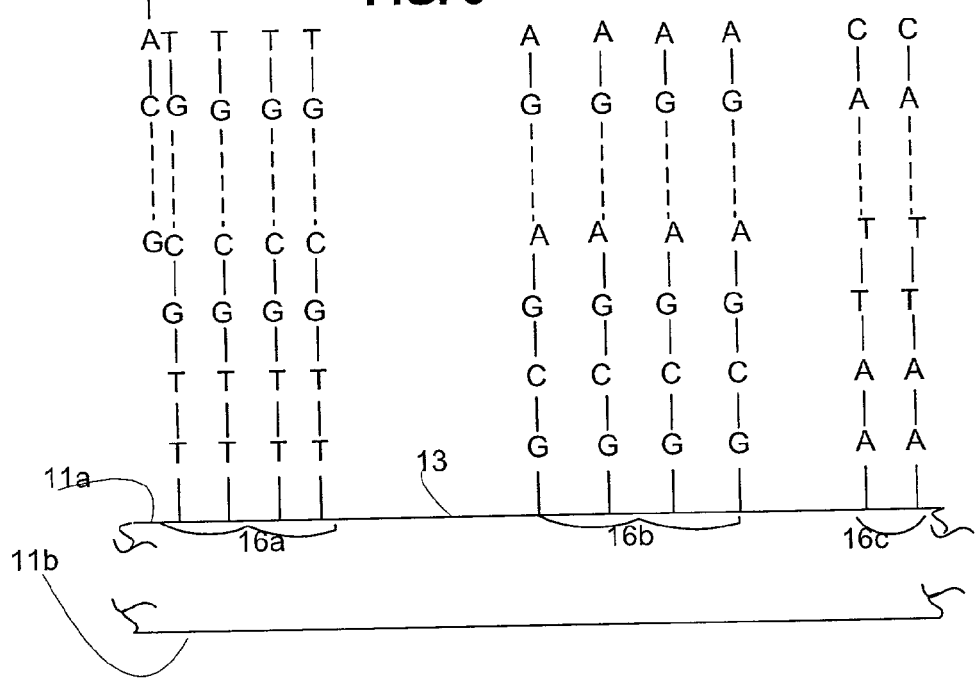
FIG. 3 is an enlarged cross-section of a portion of FIG. 2.

Referring first to FIGS. 1–3, a contiguous planar transparent substrate 10 carries multiple features 16 disposed across a first surface 11a of substrate 10 and separated by interfeature areas 13. Features 16 are disposed in a pattern which defines the array. A second surface 11b of substrate 10 does not carry any features. Substrate 10 may be of any shape although the remainder of any package carrying substrate 10, and the apparatus of the present invention, may need to be adapted accordingly. A typical array may contain at least ten features 16, or at least 100 features, at least 1,000, at least 100,000 features, or more. All of the features 16 may be of different composition, or some could be the same (for example, when any repeats of each feature composition are excluded the remaining features may account for at least 5%, 10%, or 20% of the total number of features). Each features carries probes in the form of a one moiety or mixture of moieties, which in the case of each feature 16 in FIGS. 1–3 is a polynucleotide having a particular sequence, while interfeature areas 13 do not carry any moieties of a type the same as the features 16 (for example, no polynucleotides in the case of features 16 carrying polynucleotides). This is illustrated schematically in FIG. 3 where regions 16 are shown as carrying different polynucleotide sequences. Features 16 may have widths (that is, diameter, for a round spot) of at least 5 or 10 µm, and less than 1.0 cm. In embodiments where very small spot sizes or feature sizes are desired, each of the features 16 may have widths of at least 1.0 µm and less than 1.0 mm, usually less than 500 µm, and more usually less than 200 µm. Features which are not round may have areas equivalent to the area ranges of round features 16 resulting from the foregoing diameter ranges. The probes of features 16 are typically linked to substrate 10 through a suitable linker, not shown.

The array 12 may cover an area of less than 100 $cm^2$, or even less than 50, 10 or 1 $cm^2$. In many embodiments, substrate 10 will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm.

An array identifier 40 in the form of a bar code in FIG. 1, is associated with the array 12, by being provided on the same substrate 10 adjacent one of the arrays 12. In the case where more than one array 12 is present on the same substrate 10, a separate identifier can be provided adjacent each corresponding array 12 if desired. Identifier 40 may either contain information on the layout of array 12 or be linkable to a file containing such information in a manner such as described in U.S. Pat. No. 6,180,351. Each identifier 40 for different arrays may be unique so that a given identifier will likely only correspond to one array 12 or to arrays 12 on the same substrate 10. This can be accomplished by making identifier 40 sufficiently long and incrementing or otherwise varying it for different arrays 12 or arrays 12 on the same substrate 10, or even by selecting it to be globally unique in a manner in which globally unique identifiers are selected as described in U.S. Pat. No. 6,180,351.

Arrays such as those of FIGS. 1–3 can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, other array fabrication method may be used such as described in U.S. Pat. No. 5,599,695, U.S. Pat. No. 5,753,788, and U.S. Pat. No. 6,329,143. Interfeature areas 13 need not be present particularly when the arrays are made by light directed methods as described in those patents. In use, a feature can detect a polynucleotide of a complementary sequence by hybridizing to it, such as polynucleotide 18 being detected by feature 16a in FIG. 3 (the "*" on polynucleotide 18 indicating a label such as a fluorescent label). Use of arrays to detect particular moieties in a sample (such as target sequences) are well known. The layer thickness of the probes at features 16, together with any detected target to which they are bound, is often less than 500 nm thick, and often less than 200, 100, 50 or 20 nm in thickness.

Figure 4:
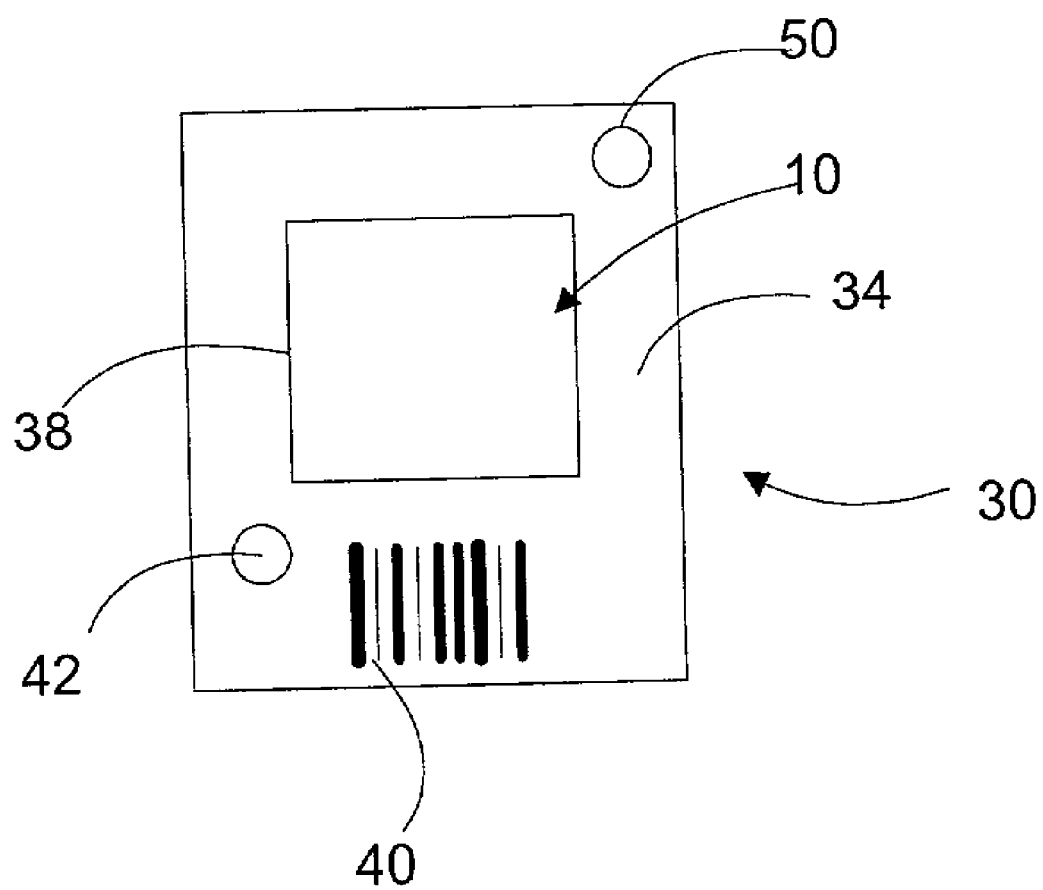
FIG. 4 is a front view of another array package in the form of a cartridge, which may be used in the present invention.

Referring now to FIG. 4 an array package 30 may include a housing 34 which has received substrate 10 adjacent an opening. Substrate 10 is sealed (such as by the use of a suitable adhesive) to housing 34 around a margin 38 with the second surface 11b facing outward. Housing 34 is configured such that housing 34 and substrate 10, define a chamber into which features 16 of array 12 face. This chamber is accessible through resilient septa 42, 50 which define normally closed ports of the chamber. In this case array package 30 may be associated with the identifier 40 by providing identifier 40 on housing 34. Throughout this application "association" of any these or other items with the array, can be accomplished, for example, by the items being present in the same package as the array when shipped to an end user.

The components of the embodiments of either array package 30 described above, may be made of any suitable material. For example, housing 34 can be made of metal or plastic such as polypropylene, polyethylene or acrylonitrile-butadiene-styrene ("ABS"). Substrate 10 may be of any suitable material, and is preferably sufficiently transparent to the wavelength of an interrogating and array emitted light, as to allow interrogation without removal from housing 34. Such transparent and non-transparent materials include, for flexible substrates: nylon, both modified and unmodified, nitrocellulose, polypropylene, and the like. For rigid substrates, specific materials of interest include: glass; fused silica, silicon, plastics (for example, polytetrafluoroethylene, polypropylene, polystyrene, polycarbonate, and blends thereof, and the like); metals (for example, gold, platinum, and the like). The first surface 11a of substrate 10 may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto (for example, conjugated), The materials from which substrate 10 and housing 34 (at least the portion facing toward the inside of chamber 36) may be fabricated should ideally themselves exhibit a low level of binding during hybridization or other events.

Figure 5:
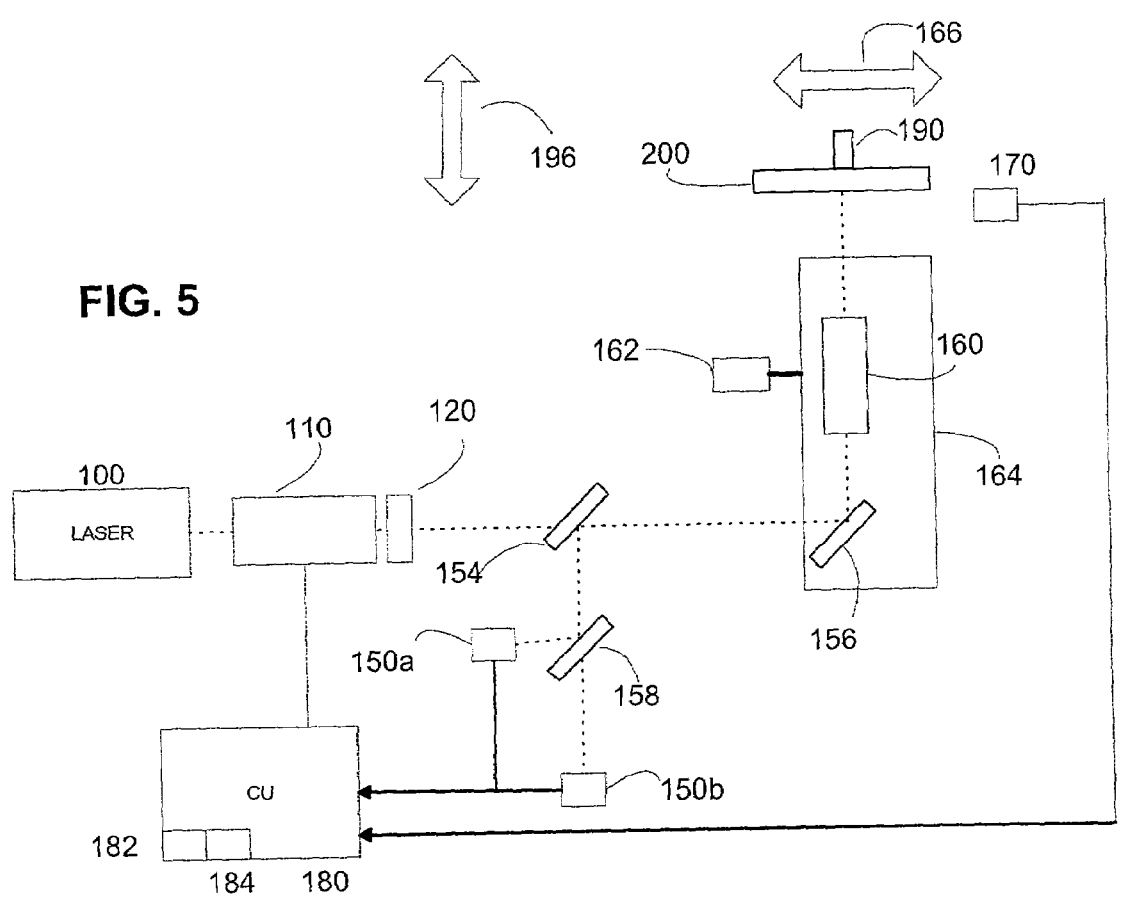
FIG. 5 schematically illustrates an apparatus of the present invention.

Referring now to FIG. 5, an apparatus of the present invention (which may be generally referenced as an array "scanner") is illustrated. A light system provides light from a laser 100 which passes through an electro-optic modulator (EOM) 110 with attached polarizer 120. A control signal in the form of a variable voltage applied to the EOM 110 by the controller (CU) 180 changes the polarization of the exiting light which is thus more or less attenuated by the polarizer 120. Controller 180 may be or include a suitably programmed processor. Thus, EOM 110 and polarizer 120 together act as a variable optical attenuator which can alter the power of an interrogating light spot exiting from the attenuator. The remainder of the light is transmitted through a dichroic beam splitter 154, reflected off fully reflecting mirror 156 and focused onto either an array 12 of an array package 30 mounted on a holder 200, or a calibration member 230, whichever is at a reading position, using optical components in beam focuser 160. Calibration member 230 is positioned to a side of holder 200 (more specifically, to a side of a mounted array therein) and is coplanar with holder 200 (more specifically with a mounted array therein). Light emitted, in particular fluorescence, at two different wavelengths (for example, green and red light) from features 16 or regions of calibration member 230, in response to the interrogating light, is imaged using the same optics in focuser/scanner 160, and is reflected off mirrors 156 and 154. The two different wavelengths are separated by a further dichroic mirror 158 and are passed to respective detectors 150a and 150b. More optical components (not shown) may be used between the dichroic and each detector 150a, 150b (such as lenses, pinholes, filters, fibers etc.) and each detector 150a, 150b may be of various different types (e.g. a photo-multiplier tube (PMT) or a CCD or an avalanche photodiode (APD)). All of the optical components through which light emitted from an array 12 or calibration member 230 in response to the illuminating laser light, passes to detectors 150a, 150b, together with those detectors, form a detection system. This detection system has a fixed focal plane.

Figure 6:
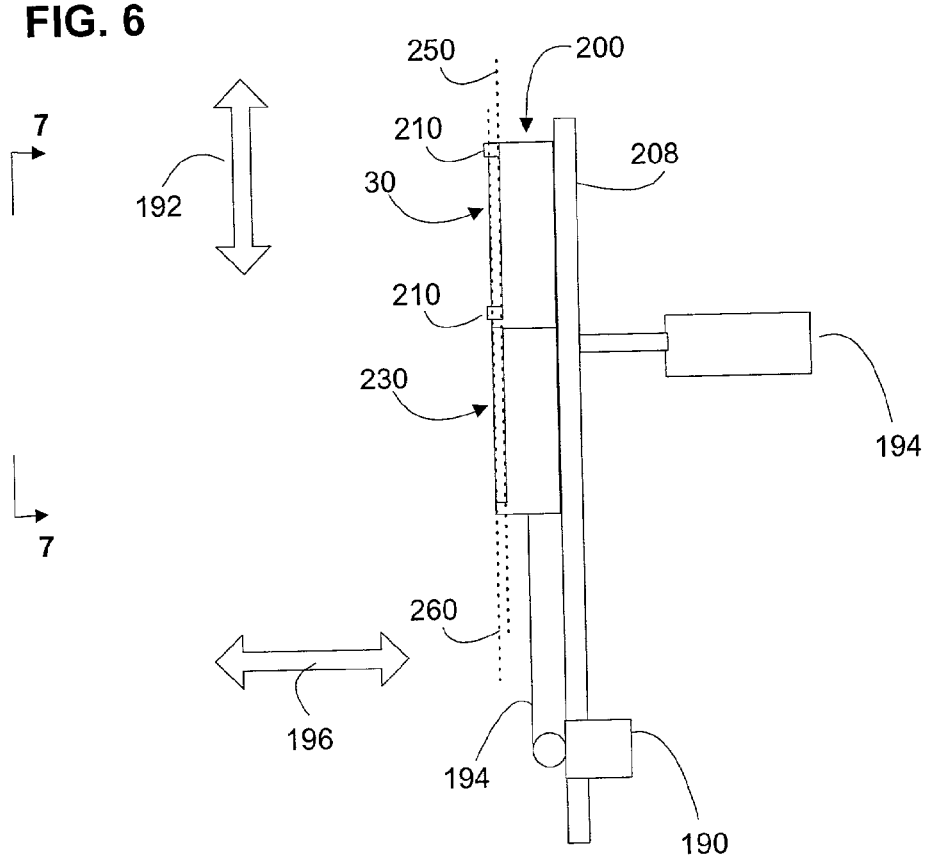
FIG. 6 illustrates components of the apparatus of FIG. 5 in more detail and is a view along the line 6—6 of FIG. 7.
Figure 7:
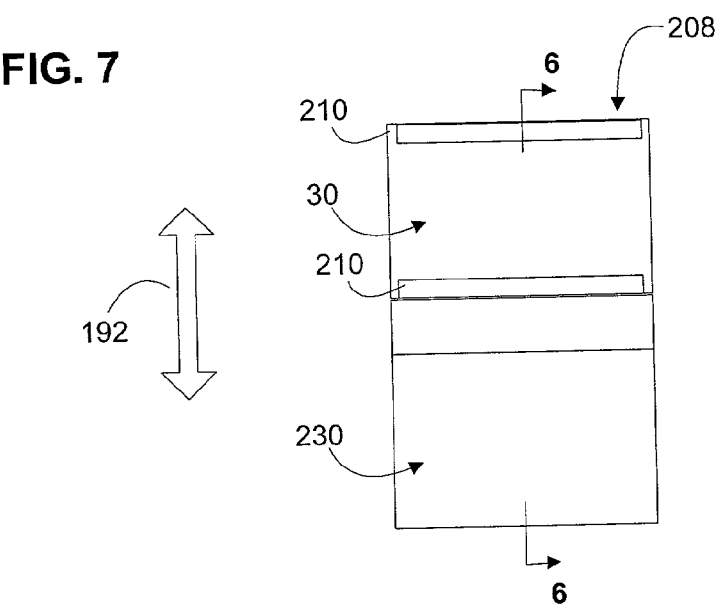
FIG. 7 is a view of components of FIG. 6 along line 7—7 of FIG. 6.

Holder 200, as shown in more detail in FIGS. 6 and 7, includes two tracks 210 open at one end such that an array package 30 can be mounted on holder 200 by sliding it inside and along tracks 210. Holder 200 may receive array package 30 with the array 12 positioned in the plane 250 (in the case where the substrate 10 is transparent and the illuminating light is to pass through substrate 10), or in the plane 260 (in the case where the illuminating light will not pass through substrate 10, whether substrate 10 is transparent or opaque to such light). Note that calibration member has a uniform layer which fluoresces at the same two detected wavelengths, and has the same thickness, as the target bound probes at features 16. Thus, the uniform fluorescent layer on calibration member 230 may have a thickness which is often less than 500 nm thick, and often less than 200, 100, 50 or 20 nm thick. Calibration member 230 is positioned on holder 200 such that its fluorescent layer is coplanar with array features 16, that is either at plane 250 or 260, as illustrated in FIG. 6. In the case where calibration member 230 is positioned at plane 250 (illuminating through a transparent substrate 10 of package 30) the calibration member 230 may itself also have a same substrate coplanar with substrate 10 of a mounted array. A suitable uniform fluorescent layer could, for example, be constructed by providing a uniform coating on a glass substrate of polymethylmethacrylate ("PMMA") of from about 0.4 to 1 microns in thickness containing cyanine dyes Cy3 and Cy5.

An adjuster 194 is further provided to adjust the position of calibration member 230 and a mounted array 12, relative to the detection system focal plane. That is, adjuster 194 can move holder 200 in the directions of arrow 196 as shown in FIGS. 5 and 6.

A scan system causes the illuminating region in the form of a light spot from laser 100, and a detecting region of each detector 150a, 150b (which detecting region will form a pixel in the detected image), to be scanned across multiple regions of an array package 30 mounted on holder 200 or multiple regions of calibration member 230. The scanned regions for an array 12 will include at least the multiple features 16 of the array. In particular the scanning system is typically a line by line scanner, scanning the interrogating light in a line across an array 12, or calibration member 230, whichever is at the reading position, in a direction of arrow 166, then moving ("transitioning") the interrogating light in a direction 192 (see FIG. 6; this direction is into/out of the paper in FIG. 5) to a position at an end of a next line, and repeating the line scanning and transitioning until the entire array 12 or calibration member 230 has been scanned. This can be accomplished by providing a housing 164 containing mirror 158 and focuser 160, which housing 164 can be moved along a line of pixels (that is, from left to right or the reverse as viewed in FIG. 5) by a transporter 162. The second direction 192 of scanning (line transitioning) can be provided by second transporter which includes a motor 190 and belt 194 to move holder 200 along one or more tracks 208 (only one shown in FIG. 6). The second transporter may use a same or different actuator components to accomplish coarse (a larger number of lines) movement and finer movement (a smaller number of lines). The second transporter also functions as a carriage, which alternately positions the mounted array and the calibration member into the reading position, as best seen in FIG. 6. In FIG. 6, calibration member 230 is in the reading position. The reader of FIG. 5 may further include a reader (not shown) which reads an identifier 40 from an array package 30. When identifier 40 is in the form of a bar code, that reader may be a suitable bar code reader.

An autofocus detector 170 is also provided to sense any offset between different regions of array 12 when in the reading position, and a determined position of the focal plane of the detection system. An autofocus system includes detector 170, processor 180, and adjuster 194 operating together as described below. A suitable chemical array autofocus system is described in pending U.S. patent application Ser. No. 09/415,184 for "Apparatus And Method For Autofocus " by Dorsel et al., filed Oct. 7, 1999, incorporated herein by reference, as well as European publication EP 1091229 published Apr. 11, 2001 under the same title and inventors.

Controller 180 of the apparatus is connected to receive signals from detectors 150a, 150b (these different signals being different "channels"), namely a signal which results at each of the multiple detected wavelengths from emitted light for each scanned region of array 12 or calibration member 230 (depending upon which one is at the reading position). Controller 180 also receives the signal from autofocus offset detector 170, and provides the control signal to EOM 110, and controls the scan system (including those components which also function as the carriage) and adjuster. Controller 180 may also analyze, store, and/or output data relating to emitted signals received from detectors 150a, 150b in a known manner. Controller 180 may include a computer in the form of a programmable digital processor, and include a media reader 182 which can read a portable removable media (such as a magnetic or optical disk), and a communication module 184 which can communicate over a communication channel (such as a network, for example the internet or a telephone network) with a remote site (such as a database at which information relating to array package 30 may be stored in association with the identification 40). Controller 180 is suitably programmed to execute all of the steps required by it during operation of the apparatus, as discussed further below. Alternatively, controller 180 may be any hardware or hardware/software combination which can execute those steps.

In one mode of operation, the array in package 30 is typically first exposed to a liquid sample (for example, placed directly on substrate 10 or introduced into a chamber through one of the septa 42, 50). The array may then be washed and scanned with a liquid (such as a buffer solution) present in the chamber and in contact with the array, or it may be dried following washing. Following a given array package 30 being mounted in the apparatus, the identifier reader may automatically (or upon operator command) read array ID 40, and use this to retrieve information on the array layout. Such information may be retrieved directly from the contents of identifier 40 when ID 40 contains such information. Alternatively, identifier 40 may be used to retrieve such information from a database containing the identifier in association with such information. Such a database may be a local database accessible by controller 180 (such as may be contained in a portable storage medium in drive 182 which is associated with package 30, such as by physical association with package 30 when received by the user, or by a suitable identification), or may be a remote database accessible by controller 180 through communication module 184 and a suitable communication channel (not shown).

Figure 8:
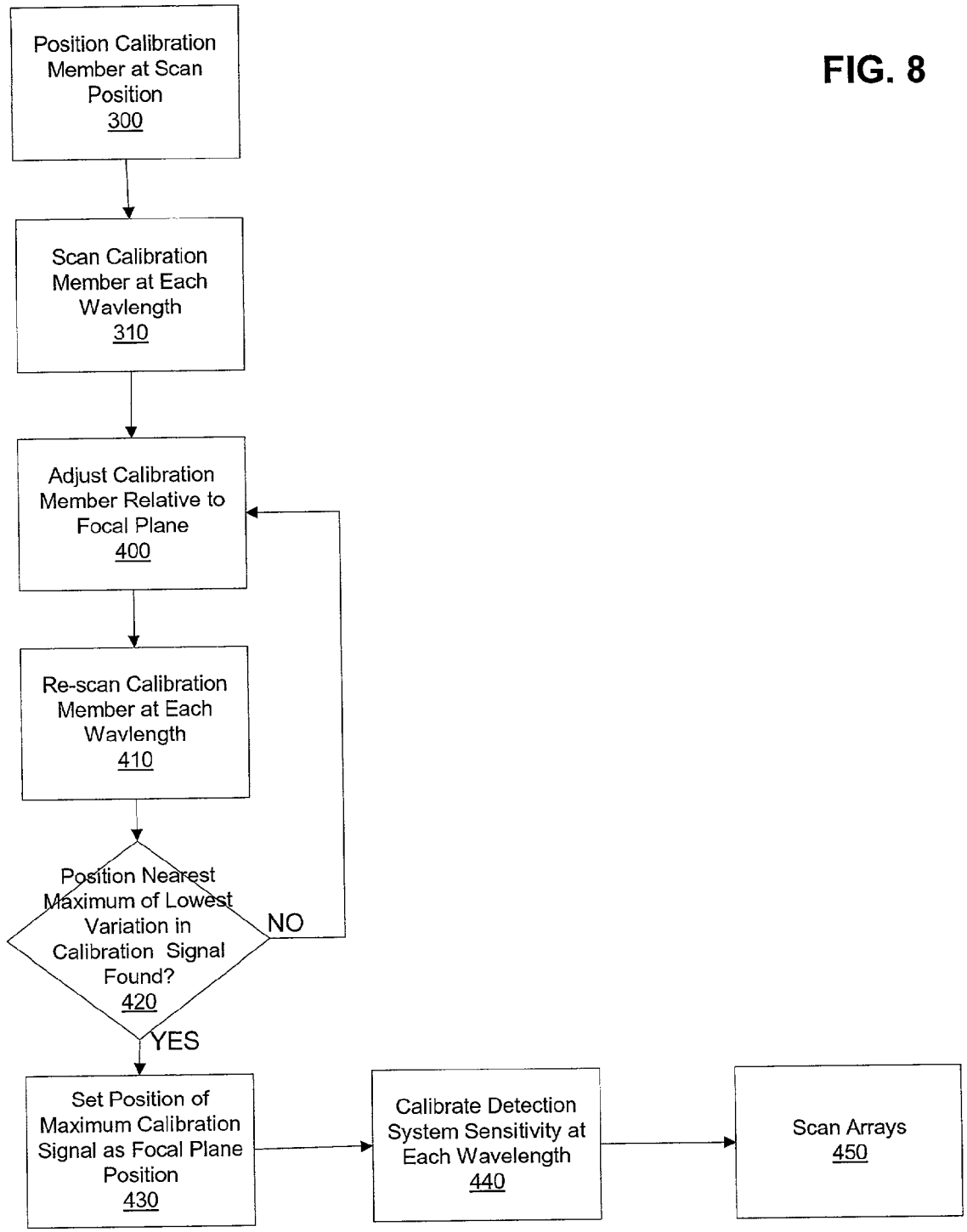
FIG. 8 is a flowchart of a method of the present invention.

Further sequence of operation may be understood particularly with reference to FIG. 8. Numbers in parentheses refer to FIG. 8. First controller 180 controls the carriage (specifically by controlling motor 190) to position (300) calibration member 230 at the reading position, as shown in FIG. 6. The calibration member 230 is then scanned (310) by the scan system, with the signals for each of the two wavelengths for each scanned region of calibration member 230 being received by controller 180. Each such received signal is based on total detected light amplitude at the corresponding detectors 150a, 150b. Controller 180 then, averages all calibration member 230 signals within each channel and saves the results in memory. Note that the detected light amplitude in each channel from the multiple scanned regions of the calibration member, will be the same when each is at the focal plane (since the fluorescent layer of calibration member 230 is uniform, as previously mentioned). Controller 180 then activates adjuster 190 to adjust (400) the position of calibration member 230 relative to the focal plane. The amount of adjustment can be programmed to initially be in either direction of arrow 196. Controller 180 then re-scans 410 the calibration member at each wavelength and generates the same average signal as previously mentioned. The averages from either one of the channels may be compared and the adjusting (400) and re-scanning (410) repeated multiple times. Alternatively, the adjustment of adjuster 190 can be varied during a same single scan. As data on calibration signal versus the adjusted position of the calibration member are collected, it is examined until enough data is collected to identify (420) the position nearest the maximum calibration signal, at which the calibration signal has the lowest variation with respect to position change (that is, closest to zero slope or, put another way, least sensitivity to change in position). This position of least variation is typically evaluated over some pre-selected range (for example, 2 µm up to 8 µm). In other words, the position of least variation is that position nearest the maximum calibration signal which, over the selected range, appears flattest on a graph of calibration signal versus calibration member position. When the signal which is flattest over the pre-selected range is identified, the middle of the corresponding calibration member position adjustment range is then set (430) as the determined focal plane position. This determined position will typically be close to the position which provides the maximum calibration signal, but they may not be identical. The average maximum signal for each channel can then be used to calibrate the detection system sensitivity in the corresponding channel since calibration member 230 should yield the same signal in a channel over time. This method of calibrating the scanner accounts for changes in signal due to changes of any part of the system: detector sensitivity, alignment of the illumination optics, alignment of the detection optics, deterioration of any optical components. However, it will be appreciated that calibration member 230 may have to be replaced from time to time due to fading of fluorescent dyes therein (for example Cy3 and Cy5 fluorescent dyes). Calibration may be accomplished by adjusting the sensitivity of detectors 150a, 150b (such as adjusting voltage in a PMT) or by adjusting gain in any attached amplifier circuit (not shown).

If the desired reading position of the array, determined as described above, is significantly different for the different wavelength channels, this will indicate a misalignment of the optical system. The system can be programmed to report an error to the user if the misalignment is seen to deviate beyond a preselected value representing the expected range of normal use. This report could prompt the user to have the scanner serviced.

Following the above processor 180 may then use adjuster 194 to move plane 250 or 260 into the focal plane (if needed), an array package 30 mounted in holder 200 (if not already present) and array 12 scanned. Further arrays 12 may be scanned by placing each in turn in holder 200. During reading, the detection system will detect light from the different regions across the array 12 emitted in response to the illumination, and generate a resulting signal for each of the regions across the array which can be stored or analyzed by controller 180, as already mentioned.

The saved results from a sample exposed array, read according to a method of the present invention, may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication of data representing the results) to a remote location if desired, and received there for further use (such as further processing).

Note that a variety of geometries of the features 16 may be constructed other than the organized rows and columns of the array of FIGS. 1–3. For example, features 16 can be arranged in a series of curvilinear rows across the substrate surface (for example, a series of concentric circles or semi-circles of spots), and the like. Even irregular arrangements of features 16 can be used, at least when some means is provided such that during their use the locations of regions of particular characteristics can be determined (for example, a map of the regions is provided to the end user with the array). Furthermore, substrate 10 could carry more than one array 12, arranged in any desired configuration on substrate 10. While substrate 10 is planar and rectangular in form, other shapes could be used with housing 34 being adjusted accordingly. In many embodiments, substrate 10 will be shaped generally as a planar, rectangular solid, having a length in the range about 4 mm to 200 mm, usually about 4 mm to 150 mm, more usually about 4 mm to 125 mm; a width in the range about 4 mm to 200 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. However, larger substrates can be used. Less preferably, substrate 10 could have three-dimensional shape with irregularities in first surface 11a. In any event, the dimensions of housing 34 may be adjusted accordingly. Additionally, during scanning it is possible to illuminate all pixels of a line simultaneously (for example, by using a line of light emitting diodes).

It will also be appreciated that focal plane determinations can be made from resulting signals at various adjusted positions of calibration member 230, taken from just one region. However, scanning the calibration member 230 in the same pattern as an array 12 allows the use of a same procedure for scanning either. Calibration member 230 may also be mounted in holder 200 in a similar manner as an array package 30, allowing for easy mounting thereon and replacement as needed. With the present invention, controller 180 can be conveniently programmed to automatically re-determine the position of the focal plane and/or re-calibrate the detection system on each channel, from time to time (for example, after a fixed time or number of arrays scanned). The apparatus and methods of the present invention may also be applied to chemical array readers which do not have an autofocus system.

Other various modifications to the particular embodiments described above are, of course, possible. Accordingly, the present invention is not limited to the particular embodiments described in detail above.

What is claimed is:

1. A method using a chemical array reader having:
   i) a holder to mount an array and hold the array at a reading position;
   ii) a light system to illuminate a mounted array when at a reading position;
   iii) a detection system having a focal plane, to detect light from different regions across the array emitted in response to the illumination, when at the reading position, and which generates a resulting signal for each of the regions across the array; and
   iv) an autofocus system which detects and reduces offset between the different regions of an array at the reading position and a determined position of the focal plane;
   the method comprising:
   a) positioning a calibration member having a uniform fluorescent layer at the reading position so as to receive illumination from the light system and emit light in response thereto, which emitted light is detected by the detection system to generate a resulting calibration signal;
   b) adjusting a position of the calibration member, when in the reading position, relative to the focal plane;
   c) determining the position of the focal plane from the light detected at various adjustments; and
   d) calibrating a sensitivity of the detection system from the detection system signals generated from the calibration member.

2. A method according to claim 1 wherein the focal position is determined based on a variation in detected light amplitude from the same region of the calibration member 6r from multiple regions of the calibration member from which the detected light is the same when at the focal plane, which variation results from the adjustment of the calibration member relative to the focal plane.

3. A method according to claim 2 wherein the emitted light is the same from each of the detected regions of the calibration member.

4. A method according to claim 1 wherein the position of the calibration member and the holder, relative to the focal plane, are simultaneously adjusted.

5. A method according to claim 1 wherein the detection system detects light at multiple wavelengths from the calibration member or array, when either is at the reading position, and generates a resulting signal for each of multiple detected wavelengths for a region of the calibration member and each of the regions across the array, and wherein the method comprises positioning a calibration member in (a) which emits light at the multiple wavelengths in response to illumination from the light system.

6. A method according to claim 1 wherein the light system illuminates a region and the detection system detects from a region, and the reader additionally comprises a scan system which simultaneously scans the illuminated and detected regions across the different regions of the array when at the reading position.

7. A method according to claim 6 wherein the scan system additionally scans the illuminated and: detected regions across different regions of the calibration member when at the reading position, such that the detection system generates resulting signals for each of the different regions across the calibration member, which are used to determine the focal plane position.

8. A method according to claim 1 additionally comprising:
   reading an array by positioning the array at the reading position such that the detection system detects light from different regions across the array emitted in response to the illumination and generates a resulting signal for each of the regions across the array.

9. A method according to claim 8 wherein the data is communicated to a remote location.

10. A method comprising receiving data representing a result of a reading obtained by the method of claim 8.

11. A method according to claim 1 wherein the uniform fluorescent layer of the calibration member is positioned coplanar to the light emitting regions across the array.

12. A method according to claim 11 wherein the calibration member comprises a substrate that is the same as that of the array.

13. A method according to claim 12 wherein the calibration member substrate is positioned coplanar to the array substrate.

14. A method according to claim 1 wherein the uniform fluorescent layer of the calibration member is the same thickness as the light emitting regions across the array.

15. A method according to claim 1 wherein the uniform fluorescent layer of the calibration member comprises more than one fluorescent dye.

16. A method according to claim 15 wherein the uniform fluorescent layer of the calibration member comprises the fluorescent dyes Cy3 and Cy5.

17. A method of using a chemical array reader, the method comprising:
   a) providing a calibration member comprising a substrate with at least one calibrating region thereon;
   b) providing a chemical array comprising a substrate with at least one chemical feature region thereon;
   c) calibrating the chemical array reader using the calibration member by a method comprising:
      i) positioning the calibration member at a reading position of the chemical array reader;
      ii) illuminating the calibration member with light from a light system of the chemical array reader;
      iii) detecting light emitted from the calibration member in response to the illuminating light with a detection system of the chemical array reader to generate a resulting calibration signal;
      iv) adjusting: the position of the calibration member relative to the detection system;
      v) repeating steps (ii) to (iv) until a focal plane of the detection system can be determined from the calibration signals generated at various adjustments: and
      vi) calibrating at least one sensitivity setting of the detection system from the calibration signals generated from the calibration member when positioned at the focal plane of the detection system; and
   d) reading the chemical array using the calibrated chemical array reader by the method comprising:
      i) positioning the chemical array at the focal plane of the detection system:
      ii) detecting light emitted from different regions across the chemical array in response to illuminating the chemical array with light from the light system; and
      iii) generating a resulting data signal for each of the detected regions across the army.

18. A method according to claim 17 wherein the calibrating region of the calibration member is positioned coplanar to the chemical feature region on the chemical array.

19. A method according to claim 17 wherein the calibration member comprises a substrate that is the same as that of the chemical array.

20. A method according to claim 17 wherein the calibration member substrate is positioned coplanar to the array substrate.

21. A method according to claim 17 wherein the calibrating region on the calibration member comprises a uniform fluorescent layer.

22. A method according to claim 21 wherein the uniform fluorescent layer of the calibration member is the same thickness as the chemical feature region on the array.

23. A method according to claim 21 wherein the uniform fluorescent layer of the calibration member comprises more than one fluorescent dye.

24. A method according to claim 23 wherein the uniform fluorescent layer of the calibration member comprises the fluorescent dyes Cy3 and Cy5.

25. A method according to claim 17 wherein the data is communicated to a remote location.

26. A method comprising receiving data representing a result of a reading obtained by the method of claim 17.

* * * * *